US010869922B2

(12) United States Patent
Wei et al.

(10) Patent No.: US 10,869,922 B2
(45) Date of Patent: Dec. 22, 2020

(54) ALHYDROGEL-SODIUM CHLORIDE COMPOUND IMMUNOLOGIC ADJUVANT, PREPARATION METHOD AND USE THEREOF

(71) Applicant: SICHUAN UNIVERSITY, Chengdu (CN)

(72) Inventors: Xiawei Wei, Chengdu (CN); Min Luo, Chengdu (CN); Yuquan Wei, Chengdu (CN)

(73) Assignee: SICHUAN UNIVERSITY, Chengdu (CN)

( * ) Notice: Subject to any disclaimer, the term of this patent is extended or adjusted under 35 U.S.C. 154(b) by 0 days.

(21) Appl. No.: 16/300,295

(22) PCT Filed: Oct. 14, 2016

(86) PCT No.: PCT/CN2016/102131
§ 371 (c)(1),
(2) Date: Nov. 9, 2018

(87) PCT Pub. No.: WO2017/193535
PCT Pub. Date: Nov. 16, 2017

(65) Prior Publication Data
US 2019/0134191 A1    May 9, 2019

(30) Foreign Application Priority Data

May 13, 2016   (CN) .......................... 2016 1 0318724

(51) Int. Cl.
*A61K 51/00*          (2006.01)
*A61K 45/00*          (2006.01)
(Continued)

(52) U.S. Cl.
CPC ............ *A61K 39/39* (2013.01); *A61K 9/0019* (2013.01); *A61K 39/0011* (2013.01);
(Continued)

(58) Field of Classification Search
None
See application file for complete search history.

(56) References Cited

U.S. PATENT DOCUMENTS

| 9,969,984 B2 * | 5/2018 | Fan .......................... C12N 7/00 |
| 2008/0199491 A1 | 8/2008 | Brandon et al. |
| 2019/0134191 A1 | 5/2019 | Wei et al. |

FOREIGN PATENT DOCUMENTS

| CN | 101513526 A | 8/2009 |
| CN | 102349996 A | 2/2012 |

(Continued)

OTHER PUBLICATIONS

Depaz et al., "Formulation of botulinum neurotoxin heavy chain fragments for vaccine development; mechanisms of adsorption to an aluminum-containing adjuvant," Vaccine 23: 4029-4035 (Year: 2005).*

(Continued)

*Primary Examiner* — M Franco G Salvoza
(74) *Attorney, Agent, or Firm* — Caesar Rivise, PC

(57) ABSTRACT

The invention belongs to the field of biological medicine, in particular refers to an alhydrogel-sodium chloride compound immunologic adjuvant, preparation method and use thereof. The technical problem to be solved by the invention is to provide a well-behaved and novel immunologic adjuvant. The technical solution for solving the technical problem of the invention is to provide the use of sodium chloride in preparing immunologic adjuvant and the alhydrogel-sodium chloride compound immunologic adjuvant obtained on the basis thereof. The compound immunologic adjuvant (Continued)

mainly includes alhydrogel and sodium chloride. The alhydrogel-sodium chloride compound immunologic adjuvant of the invention is an excellent compound immunologic adjuvant, which can be used for various antigens, and provides a new and effective choice for the development and application of vaccines due to the advantages of simple and convenient use, low cost, strong immune activity, high clinical safety and the like.

16 Claims, 12 Drawing Sheets

(51) Int. Cl.
  *A61K 39/39* (2006.01)
  *A61K 39/02* (2006.01)
  *A61K 39/12* (2006.01)
  *A61K 39/29* (2006.01)
  *A61K 9/00* (2006.01)
  *A61K 39/00* (2006.01)

(52) U.S. Cl.
  CPC .............. *A61K 39/02* (2013.01); *A61K 39/12* (2013.01); *A61K 39/29* (2013.01); *A61K 2039/55505* (2013.01); *A61K 2039/62* (2013.01); *A61K 2039/64* (2013.01)

(56) References Cited

FOREIGN PATENT DOCUMENTS

| | | |
|---|---|---|
| CN | 102526724 A | 7/2012 |
| CN | 103705914 A | 4/2014 |
| CN | 105999260 A | 10/2016 |
| WO | 2012177970 A1 | 12/2012 |

OTHER PUBLICATIONS

Lin et al., "Considerable Differences in Vaccine Immunogenicities and Efficacies Related to the Diluent Used for Aluminum Hydroxide Adjuvant," Clinical and Vaccine Immunology, vol. 15, No. 3: 582-584 (Year: 2008).*
Yau et al., "Aluminum Hydroxide Adjuvant Produced under Constant Reactant Concentration," Journal of Pharmaceutical Sciences, vol. 95, No. 8: 1822-1833 (Year: 2006).*
Watkinson et al. ("Increasing the Potency of an Alhydrogel Formulated Vaccine by Minimising Antigen-Adjuvant Interactions," Clin. Vaccine Immunol., 20(11): 1659-1668 (Year: 2013).*
Hu et al., "Immunization Delivered by Lentiviral Vectors for Cancer and Infectious Diseases", Immunol. Rev. 239(1): 45-61 (Year: 2011).*
English Abstract for CN 101513526 A (2009).
English Abstract for CN 102349996 A (2012).
English Abstract for CN 102526724 A (2012).
English Abstract for CN 103705914 A (2014).

* cited by examiner a b

ALHYDROGEL-SODIUM CHLORIDE COMPOUND IMMUNOLOGIC ADJUVANT, PREPARATION METHOD AND USE THEREOF

CROSS-REFERENCE TO RELATED APPLICATIONS

This application is a U.S. National Phase Application of PCT/CN2016/102131, filed Oct. 14, 2016, which claims priority to 201610318724.X, filed May 13, 2016, the contents of which applications are incorporated herein by reference in their entireties for all purposes.

FIELD OF INVENTION

The invention belongs to the field of biological medicine, in particular refers to an alhydrogel-sodium chloride compound immunologic adjuvant, preparation method and use thereof.

BACKGROUND OF THE INVENTION

As a non-specific immunopotentiator, adjuvant has been used for improving the body's immune response to vaccine antigens for decades. The purpose of adding adjuvant to the vaccine is to enhance the body's immune response to the antigen or to change the type of immune response, which is manifested by promoting specific humoral immunity and/or cellular immunity of the antigen, so as to increase the production of specific antibodies or/and specific cellular immune function. Injecting antigen and adjuvant into the body together can reduce the amount of antigen and the frequency of effective immunization and improve the success rate of early immune response and the response of immunocompromised people.

The aluminum adjuvant represented by aluminum hydroxide and aluminum phosphate is still the legal vaccine adjuvant for human use approved by authorities in China. Moreover, aluminum hydroxide is also the only human adjuvant approved by the U.S. FDA. The mechanism of action of aluminum adjuvant is still not completely clear, despite its long history in use. It is currently contemplated that there are two mechanisms, i.e. "stock effect" and "immunostimulation effect". The antigen is absorbed by the aluminum adjuvant to form an antigen depot in the inoculation area where the non-specific immune stimulation attracts the recognition and endocytosis of antigen presenting cells (APC) such as dendritic cells and macrophages; and the sustained release of antigen at the injection site prolongs the interaction time between APC and T lymphocytes, thus improving antibody response and enhancing humoral immunity.

Sodium chloride plays an important role in the life on earth, and it is widely used in daily life, industry and medicine. In addition, it is the main component of salt needed for diet in daily life and saline injection used in medicine. Furthermore, it has the advantages of easy access, low price and high safety.

With the rapid development of novel adjuvants, traditional adjuvants have become increasingly unable to meet the needs of vaccines. A large number of immunologic clinical trials reveal that aluminum hydroxide colloid adjuvant has a strong stimulating effect on humoral immune response, but a weak effect on cellular immune response. How to improve cellular immunity mediated by aluminum adjuvant, which can effectively induce the body to produce both the humoral and the cellular immunity is therefore the focus and difficulty of current research on immunologic adjuvant.

At present, sodium chloride has not yet been combined with aluminum hydroxide as a compound immunologic adjuvant. Thus, a novel and well-behaved immunologic adjuvant is urgently needed in the art to give a new and effective choice for vaccine preparation.

SUMMARY OF THE INVENTION

The technical problem to be solved by the invention is to provide a novel and well-behaved immunologic adjuvant, which can give a new and effective choice in the art.

The technical scheme for solving the technical problem of the invention is to provide a compound immunologic adjuvant mainly comprising alhydrogel and sodium chloride which is higher than physiological level.

Wherein, the dosage of sodium chloride in immunologic adjuvant is higher than physiological level, which means that the mass fraction of sodium chloride in the final adjuvant-antigen complex solvent is more than 0.9%. The final mass fraction refers to the concentration of immunologic adjuvant-antigen complex before injection.

Wherein, the final mass fraction of the sodium chloride in the aforementioned compound immunologic adjuvant is 1.2%-7.2%. Further, the final mass fraction of the sodium chloride in the compound immunologic adjuvant is 2.7%-4.5%. Preferably, the final mass fraction of the sodium chloride in the compound immunologic adjuvant is 3.6%.

Wherein, the final mass fraction refers to the mass (g) of sodium chloride in 100 ml of adjuvant-antigen complex solvent.

Wherein, the particle size of the alhydrogel in the compound immunologic adjuvant ranges from 1 μm, preferably 2 μm-6 μm, and more preferably about 3 μm.

The invention further provides an immunologic adjuvant-antigen complex formed by adding antigen to the compound immunologic adjuvant. The immunologic adjuvant-antigen complex may also be referred to as a vaccine in the art.

Wherein, the antigen (Ag) in the immunologic adjuvant-antigen complex is any substance capable of inducing immune response in the art.

Further, the antigen is one or more of a tumor antigen, a virus antigen or a bacterial antigen.

Wherein, the tumor antigen can be selected from one or more of OVA tumor model antigen (OVA tumor model antigen is internationally recognized as a model or standardized tumor specific antigen, and commonly used as a standard tumor specific antigen to test the ability of an adjuvant to induce an anti-tumor immune response. If the adjuvant induces an anti-tumor immune response, then the adjuvant is representative of anti-tumor immune response.), NY-ESO-1, human melanoma-associated antigen gP100, melanoma antigen mage-1 or carcinoembryonic antigen and other common tumor antigens.

Wherein, the virus antigen is selected from one or more of common virus antigens such as hepatitis B virus antigen, hepatitis A virus antigen, hepatitis C virus antigen, poliovirus antigen, rabies virus antigen, yellow fever virus antigen, HIV antigen, measles antigen, mumps antigen, rubella antigen, chicken pox antigen, rotavirus antigen, Japanese encephalitis antigen, papillomavirus antigen, epidemic hemorrhagic fever virus antigen and plague virus antigen.

Wherein, the bacterial antigen is selected from at least one of common bacterial antigens such as *Staphylococcus aureus* antigen, *Pseudomonas aeruginosa* antigen, pertussis antigen, diphtheria antigen, *Haemophilus influenzae* antigen, *Neisseria meningitidis* antigen, tetanus toxoid antigen, *Streptococcus hemolyticus* antigen, *Streptococcus non-hemolyticus* antigen, *Pneumococcus* antigen, *Tubercle bacillus* antigen, *Bacillus anthracis* antigen, *Vibrio cholerae* antigen, *leptospira* antigen or *Helicobacter pylori* antigen.

The invention further provides a method for preparing the immunologic adjuvant/antigen complex, comprising the following steps:

a diluting or dissolving the required antigen in water;

b adding the required sodium chloride, and uniformly mixing;

c adding the required amount of alhydrogel, and uniformly mixing.

Also, the immunologic adjuvant/antigen complex can be prepared by the following steps:

a adding an appropriate amount of sodium chloride to an alhydrogel adjuvant to prepare a stock solution for the hypertonic alhydrogel compound adjuvant;

b diluting or dissolving the required antigen in water;

c adding the required amount of hypertonic alhydrogel compound adjuvant, and uniformly mixing.

Further, the antigen is one or more of a tumor antigen, a virus antigen or a bacterial antigen.

Wherein, the tumor antigen is selected from one or more of common tumor antigens such as OVA tumor model antigen, NY-ESO-1, human melanoma-associated antigen gP100, melanoma antigen mage-1 or carcinoembryonic antigen.

Wherein, the virus antigen is selected from one or more of common virus antigens such as hepatitis B virus antigen, hepatitis A virus antigen, hepatitis C virus antigen, poliovirus antigen, rabies virus antigen, yellow fever virus antigen, HIV antigen, measles antigen, mumps antigen, rubella antigen, chicken pox antigen, rotavirus antigen, Japanese encephalitis antigen, papillomavirus antigen, epidemic hemorrhagic fever virus antigen and plague virus antigen.

Wherein, the bacterial antigen is selected from at least one of common bacterial antigens such as *Staphylococcus aureus* antigen, *Pseudomonas aeruginosa* antigen, pertussis antigen, diphtheria antigen, *Haemophilus influenzae* antigen, *Neisseria meningitidis* antigen, tetanus toxoid antigen, *Streptococcus hemolyticus* antigen, *Streptococcus non-hemolyticus* antigen, *pneumococcus* antigen, *Tubercle bacillus* antigen, *Bacillus anthracis* antigen, *Vibrio cholerae* antigen, *leptospira* antigen or *Helicobacter pylori* antigen.

The mass fraction in the technical scheme refers to the mass (g) of sodium chloride in 100 ml of adjuvant-antigen complex solution.

It can be understood that the invention also provides a vaccine prepared from the immunologic adjuvant-antigen complex, which may be a preventative and/or therapeutic vaccine. For example, the immunologic adjuvant-antigen complex can be prepared into a hepatitis vaccine targeting hepatitis antigen such as HBsAg, a bacterial vaccine targeting bacterial antigen such as pertussis antigen, diphtheria toxoid antigen or *Staphylococcus aureus* antigen and *Pseudomonas aeruginosa* antigen, and preventative and/or therapeutic tumor vaccine targeting OVA tumor model antigen or tumor specific antigen. The vaccine of the invention can be administered through subcutaneous, intraperitoneal, or intramuscular injection to immunize the subject. Of course, other methods available in the art or a combination of various methods can also be used for immunization. The vaccine of the invention can have different immunity intervals, and can be administered once or many times. Specifically, the immunization times and time points can be changed or adjusted according to the actual situation.

In order to construct a well-behaved aluminum hydroxide-sodium chloride compound adjuvant which can be used as an immunologic adjuvant, the invention examines various aluminum hydroxide-sodium chloride formulations. According to the invention, sodium chloride with different mass fractions is screened, and the best effect is observed when the mass fraction of sodium chloride in the vaccine solution prepared by using the sodium chloride-aluminum hydroxide compound as an adjuvant is 3.6%. The hepatitis vaccine model produces high titers of antibodies and IFN-γ against HBsAg in vivo. The bacterial vaccine produces high titers of antibodies and IFN-γ against pertussis and diphtheria toxoid, high titers of antibodies against *Staphylococcus aureus* and *Pseudomonas aeruginosa*, and protective effect against the bacterial. In terms of tumor vaccine model, preventive and therapeutic immunity experiments prove that production of antibodies against OVA and activation of specific CD8 killer T cells in vivo increase IFN-γ secretion and effectively inhibit tumor growth.

Also, the invention provides a use of sodium chloride in the preparation of immunologic adjuvant.

Wherein, the immunologic adjuvant further comprises alhydrogel.

Wherein, the dosage of the sodium chloride in the immunologic adjuvant is higher than physiological level.

Wherein, the dosage of the sodium chloride in the immunologic adjuvant is such that the mass fraction of sodium chloride in the immunologic adjuvant-antigen complex prepared therefrom is 1.2%-7.2%, which indicates the concentration of immunologic adjuvant-antigen complex before injection.

Also, the invention provides a use of sodium chloride in the preparation of immunologic adjuvant-antigen complex.

Wherein, the immunologic adjuvant-antigen complex further comprises an adjuvant of alhydrogel.

Wherein, the content of sodium chloride is 1.2%-7.2% by mass, which indicates the concentration of immunologic adjuvant-antigen complex before injection. The content of sodium chloride is preferably 2.7%-4.5% by mass, and more preferably 3.6% by mass.

Wherein, the ratio of antigen to aluminum hydroxide is 1:1-100 by weight.

Wherein, the ratio of antigen to aluminum hydroxide in compound immunologic adjuvant is 1:5-50 by weight.

Wherein, the antigen is one or more of a tumor antigen, a virus antigen or a bacterial antigen. The invention also provides a method for preparing a vaccine, comprising adding sodium chloride and a proper amount of water for injection and allowing the mass fraction of sodium chloride to reach 1.2%-7.2% before the vaccine is used. The method can be implemented in the following ways as the case may be:

adding a proper amount of water for injection and sodium chloride to antigen, then adding alhydrogel adjuvant, and allowing the mass fraction of sodium chloride in the prepared vaccine to reach 1.2%-7.2% before the vaccine is used;

or directly dissolving antigen by water for injection, adding hypertonic alhydrogel stock solution, and allowing the mass fraction of sodium chloride in the prepared vaccine to reach 1.2%-7.2%;

or directly adding sodium chloride as an adjuvant in the preparation process, and allowing the mass fraction of sodium chloride in the prepared vaccine to reach 1.2%-7.2% before injection, if the vaccine to be prepared already contains antigen and alhydrogel.

The content of sodium chloride in the vaccine system to be injected is preferably 2.7%-4.5% by mass, and more preferably 3.6% by mass.

Wherein, in the above method, the ratio of antigen in the vaccine to aluminum hydroxide is 1:1-100 by weight, and preferably 1:5-50 by weight.

It should be noted that, the ratio of the antigen to aluminum hydroxide by weight in the invention refers to the ratio of the antigen to pure aluminum hydroxide in alhydrogel.

Obviously, the sodium chloride should have the purity required for preparing a vaccine in the technical scheme. In general, at least chemically pure sodium chloride should be used.

The invention provides the use of sodium chloride in the preparation of vaccine adjuvant and vaccine. In addition, the invention also provides the novel vaccine adjuvant, namely alhydrogel-sodium chloride compound immunologic adjuvant, which can be used in the research and development of tumor vaccines and infectious disease vaccines such as bacterial and virus vaccines. Through preliminary analysis, it is found that its mechanism of action may be as follows: hypertonic sodium chloride above physiological level can activate immune cell activities such as MΦ, NK and DC, activate MAPK signaling pathway, and promote DC maturation and antigen uptake or cross presentation. Furthermore, aluminum salt in alhydrogel combines with antigen to form an antigen depot, which enables the antigen to be released slowly and stably, and aluminum adjuvant can also induce and stimulate humoral immunity. Therefore, their combination can not only stimulate humoral immunity, but also stimulate cellular immunity to achieve better results.

The beneficial effects of the invention are as follows: the invention creatively develops the use of sodium chloride in the preparation of vaccine adjuvant and vaccine, and further develops the aluminum hydroxide-sodium chloride compound immunologic adjuvant. It has the advantages of strong immune activity and high clinical safety, and can induce a specific cellular immune response compared with aluminum hydroxide alone. Thus, it is an excellent aluminum hydroxide-sodium chloride compound immunologic adjuvant against various antigens. Experiments show that the vaccine prepared by using the aluminum hydroxide-sodium chloride compound of the invention as an adjuvant can obtain better immune effect and anti-tumor effect, and provide a new choice for the development and application of various preventive and/or therapeutic vaccines.

DETAILED DESCRIPTION OF THE PREFERRED EMBODIMENT

Figure 1:
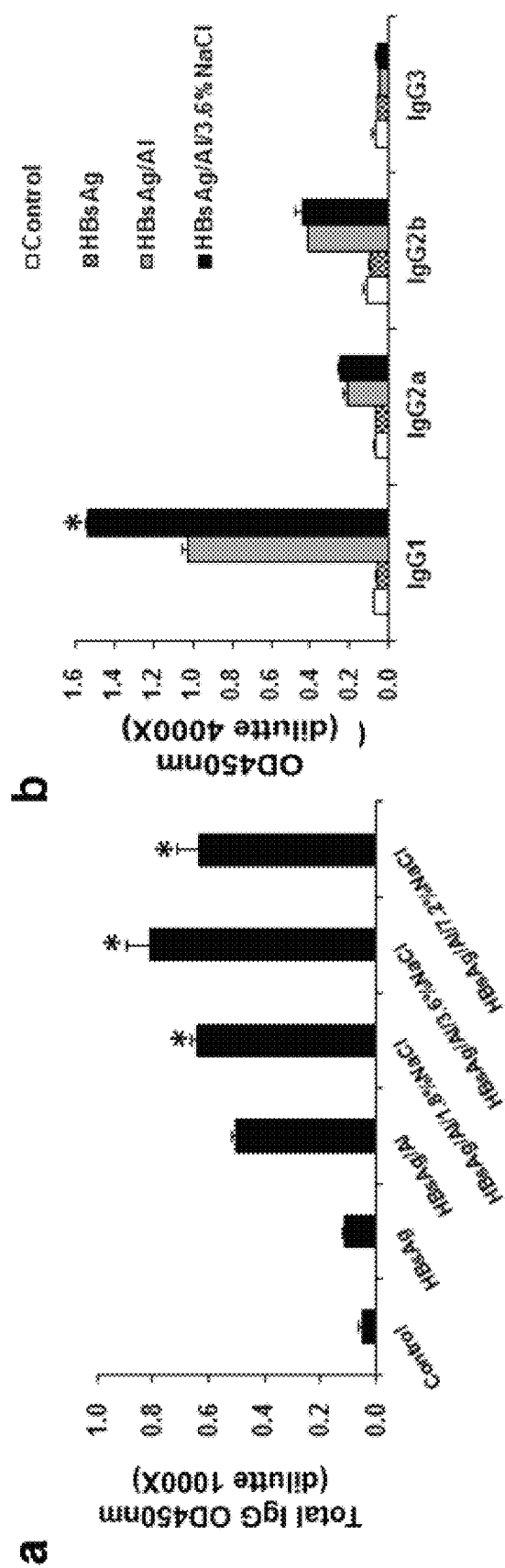
FIG. 1 shows the experimental result that the alhydrogel-sodium chloride immunologic adjuvant can enhance the serum antibody titer of each group of mice against HBsAg in the HBsAg model.

The invention will be described in detail in combination with drawings. The preparation and use of the vaccine will be further described in the following embodiments. The invention includes, but is not limited to, the specific methods and steps listed in the following embodiments.

The invention creatively finds that the sodium chloride higher than physiological level can be used as an immunologic adjuvant and used for preparing a compound immunologic adjuvant. The alhydrogel-sodium chloride complex as a compound adjuvant can effectively induce humoral immunity and cellular immunity of the body.

The compound adjuvant of the invention has two components, of which, the alhydrogel adjuvant, as a common inorganic salt adjuvant, can adsorb soluble antigens on the surface of aluminum gel molecules, concentrate the antigen and reduce the injection dose due to good protein adsorption effect. In addition, the alhydrogel is the most widely used and also the only adjuvant approved by the U.S. FDA for human vaccines as it has low cost, and is non-toxic and easy to use. Moreover, sodium chloride is widely used in daily life, industry and medicine, which is also very safe to human body and extremely low in cost.

According to further screening tests, the dosage of sodium chloride in the compound adjuvant of the invention is such that the final mass fraction of sodium chloride is greater than the physiological concentration to obtain an improved immune effect. For example, more obvious immune effect is obtained when the dosage is in the range of 1.2%-7.2%. Preferably, the immunologic adjuvant can produce better effect when the dosage is in the range of 2.7%-4.5%. In the invention, the best experimental effect is obtained at the dosage of 3.6%. The mass fraction of sodium chloride in the invention refers to the mass (g) of sodium chloride in 100 ml of antigen-adjuvant complex solvent. Obviously, according to the disclosure of the invention, it is known to those skilled in the art that the concentration of sodium chloride in the system can be changed through lyophilization, evaporation or dilution during the preparation of the vaccine according to the standards in the above scheme, but the technology that the concentration of sodium chloride in the system needs to be adjusted within the above range before it is officially used, and shall clearly fall into the protection scope of the invention.

It is known to those skilled in the art from the above description that the novel alhydrogel-sodium chloride adjuvant of the invention is an immunologic adjuvant with wide application range and safe use, and can be added to various antigens known in the art to obtain immunologic adjuvant-antigen complex for further use as vaccine. The antigen (Ag) of the invention refers to any substance capable of inducing an immune response in the art.

Further, the antigen is one or more of a tumor antigen, a virus antigen or a bacterial antigen.

Wherein, the tumor antigen refers to the common tumor antigen forms in the art, including protein or glycolipid components of tumor-specific antigen (TSA) or tumor-associated antigen (TAA). The tumor antigen can be selected from one or more of common tumor antigens such as NY-ESO-1, human melanoma-associated antigen gP100, melanoma antigen mage-1 or carcinoembryonic antigen.

Wherein, the virus antigen is selected from one or more of common virus antigens such as hepatitis B virus antigen, hepatitis A virus antigen, hepatitis C virus antigen, poliovirus antigen, rabies virus antigen, yellow fever virus antigen, HIV antigen, measles antigen, mumps antigen, rubella antigen, chicken pox antigen, rotavirus antigen, Japanese encephalitis antigen, papillomavirus antigen, epidemic hemorrhagic fever virus antigen and plague virus antigen. Moreover, the virus antigen may take the form of attenuated or inactivated virus, virus subunit vaccine, synthetic peptide vaccine, nucleic acid vaccine and other virus antigen forms apparent to those skilled in the art.

Wherein, the bacterial antigen is selected from at least one of common bacterial antigens such as *Staphylococcus aureus* antigen, *Pseudomonas aeruginosa* antigen, pertussis antigen, diphtheria antigen, *Haemophilus influenzae* antigen, *Neisseria meningitidis* antigen, tetanus toxoid antigen, *Streptococcus hemolyticus* antigen, *Streptococcus non-hemolyticus* antigen, *pneumococcus* antigen, *Tubercle bacillus* antigen, *Bacillus anthracis* antigen, *Vibrio cholerae* antigen, *leptospira* antigen or *Helicobacter pylori* antigen. The bacterial antigen can be in the form of dead vaccine, attenuated vaccine and virulent vaccine of various bacteria, pathogenic component toxoid of various bacteria, or various bacterial polysaccharides or bacterial polysaccharide binding antigen taking bacterial protein as carrier, etc., apparent to those skilled in the art.

According to the invention, sodium chloride adjuvant is added on the basis of aluminum hydroxide type hepatitis B vaccine or pertussis and diphtheria vaccine to obtain higher antibody titer and increased secretion of IFN-γ; and sodium chloride adjuvant is added on the basis of aluminum hydroxide type *Staphylococcus aureus* or *Pseudomonas aeruginosa* vaccine to obtain higher antibody titer and protective effect against the bacteria. Besides, a novel vaccine of OVA tumor model antigen was prepared by using the novel alhydrogel-sodium chloride adjuvant which is proven to be effective against tumor.

Aluminum hydroxide is generally used with a particle size in the range of 1 μm-10 μm, preferably 2 μm-6 μm. Of course, the preferred value of particle size of aluminum hydroxide may properly vary when it is possibly combined with different antigens, preferably about 3 μm.

After screening, the ratio of antigen to aluminum hydroxide in the compound immunologic adjuvant is 1:1-100 by weight, and preferably 1:5-50 by weight.

Obviously, those skilled in the art can reasonably adjust the mass fraction of sodium chloride within the above range when preparing vaccines with different antigens, and reasonably adjust the dosage of antigen in the compound immunologic adjuvant and the ratio of alhydrogel to antigen by weight.

However, the immunologic adjuvant-antigen complex of the invention can be prepared by the following two methods:

Method 1:
a diluting or dissolving the required antigen in water;
b adding the required sodium chloride, and uniformly mixing;
c adding the required amount of alhydrogel, and uniformly mixing.

Method 2:
a adding an appropriate amount of sodium chloride to an alhydrogel adjuvant to prepare a stock solution for the hypertonic alhydrogel compound adjuvant;
b diluting or dissolving the required antigen in water;
c adding the required amount of hypertonic alhydrogel compound adjuvant, and uniformly mixing.

For example, in the embodiment of the invention, when HBsAg, pertussis or diphtheria toxoid is used as antigen, the dosage of HBsAg, pertussis or diphtheria toxoid in the immunologic adjuvant/antigen complex is 1 μg, and the ratio of antigen to alhydrogel can be preferably 1:5-1:100 by weight, and more preferably 1:25 by weight.

When OVA is used as antigen, the dosage of OVA in the immunologic adjuvant/antigen complex is 5 μg, and the ratio of antigen to alhydrogel can be preferably 1:5-1:50 by weight, and more preferably 1:25 by weight.

The invention further develops a new method for preparing a vaccine on the basis of the above technology. The method comprises the following steps: adding sodium chloride and a proper amount of water for injection and allowing the mass fraction of sodium chloride to reach 1.2%-7.2% before the vaccine is used.

Specifically, the method can be carried out by adding a proper amount of water for injection and sodium chloride to the antigen, then adding alhydrogel adjuvant, and allowing the mass fraction of sodium chloride in the prepared vaccine to reach 1.2%-7.2%;

or directly dissolving antigen in water for injection, adding hypertonic alhydrogel stock solution, and allowing the mass fraction of sodium chloride in the prepared vaccine to reach 1.2%-7.2%;

When the vaccine to be prepared contains antigen and alhydrogel, the method comprises the steps of adding sodium chloride and a proper amount of water for injection to prepare a vaccine system to be injected before the vaccine is used, and enabling the mass fraction of sodium chloride in the vaccine system to be injected to reach 1.2%-7.2%.

In the above method, the mass fraction of sodium chloride in the vaccine system to be injected is preferably 2.7%-4.5%, and more preferably about 3.6%.

Wherein, the vaccine contains antigen and alhydrogel. Those skilled in the art have the ability to appropriately adjust the relative amount of antigen and aluminum hydroxide according to the different antigens selected and the specific usage of the vaccine. Generally, the ratio of antigen to aluminum hydroxide is 1:1-100 by weight. The alhydrogel of the invention can be an aluminum hydroxide immunologic adjuvant currently available in the market, an aluminum hydroxide colloid adjuvant currently prepared clinically according to *Chinese Pharmacopoeia*, or an aluminum hydroxide colloid that can be configured for vaccine preparation according to the requirements of the U.S. FDA or the relevant requirements of other countries.

Embodiment 1: Screening and Preparation of Compound Adjuvant

Materials and reagents: aluminum hydroxide adjuvant (alhydrogel) purchased from American InvivoGen (white suspension, 10 mg/mL, and particle size: 3 μm).

Hepatitis B surface antigen (HBsAg) purchased from American Research Products (ARP) and sodium chloride (NaCl) and Ovalbumin (OVA) purchased from American Sigma Inc. Pertussis (P7208) and diphtheria toxoid (D0564) purchased from American Sigma Inc. *Staphylococcus aureus* (S.a) or *Pseudomonas aeruginosa* (P.a) purchased from ATCC (33591 and 27853).

The immunologic adjuvant-antigen complex was prepared by the following two methods:

Method 1: a. diluting or dissolving the required antigen in water; b. adding the required sodium chloride, and uniformly mixing; c. adding the required amount of alhydrogel, and uniformly mixing.

Method 2: a. adding an appropriate amount of sodium chloride to an alhydrogel adjuvant to prepare a stock solution for the hypertonic alhydrogel compound adjuvant; b. diluting or dissolving the required antigen in water; c. adding the required amount of hypertonic alhydrogel compound adjuvant, and uniformly mixing.

After further screening tests, the final mass fraction of sodium chloride was 1.2%-7.2%, and preferably 3.6% to give play to the best effect of immunologic adjuvant. The mass fraction of sodium chloride in the invention refers to the mass (g) of sodium chloride in 100 ml of antigen-adjuvant complex solvent.

After screening, the ratio of antigen to aluminum hydroxide in the compound immunologic adjuvant was 1:1-100 by weight, and preferably 1:5 50 by weight.

When HBsAg, pertussis or diphtheria toxin was used as antigen, the dosage of HBsAg, pertussis or diphtheria toxin in the immunologic adjuvant/antigen complex was 1 μg, and the ratio of antigen to alhydrogel was preferably 1:5-1:100, and more preferably 1:25.

When OVA as used as the model tumor specific antigen, the dosage of OVA in the immunologic adjuvant/antigen complex was 5 μg, and the ratio of antigen to alhydrogel was preferably 1:5-1:50 by weight, and more preferably 1:25 by weight.

Embodiment 2: Animal Immunity Test Taking Sodium Chloride as Hepatitis B Vaccine Adjuvant in the Invention Materials and reagents: aluminum hydroxide adjuvant, sodium chloride and HBsAg the same as in embodiment 1; BALB/c mice purchased from Beijing Vital River Laboratory Animal Technology Co., Ltd.; Hepatitis B virus surface antibody assay kit (Wantai BioPharm); ELISA kit for IFN-γ (eBioscience, USA); lymphocyte separation medium (Dakewe Biotech Co., Ltd.); 70 μm nylon mesh filter (Becton, Dickinson and Company, USA); 24-well plate with round bottom (NUNK).

The experimental animals were grouped as follows: 1. Control; 2. HbsAg; 3. HbsAg/Al(OH)$_3$; 4. HbsAg/Al(OH)$_3$/1.8% NaCl; 5. HbsAg/Al(OH)$_3$/3 .6% NaCl; 6. HbsAg/Al(OH)$_3$/7.2% NaCl. Of all the groups, HBsAg was 1 μg and Al(OH)$_3$ was 25 μg; the ratio of HBsAg to Al(OH)$_3$ was 1:25 by weight, and the concentration of sodium chloride was 0, 1.8%, 3.6% and 7.2% respectively. The number of animals was five in each group. Muscle immunity was performed at week 0, 2 and 3, and serum and splenic lymphocytes were collected at week 4 for the following experiments.

(1) Detection of Antibody Titer

Total IgG and IgG subclasses antibody titers in the serum of mice in each group were assayed by ELISA kit (Wantai BioPharm). The absorbance test results of each group of serum antibody after dilution were shown in FIG. 1. The HBsAg group alone could hardly produce antibodies. The group using Al(OH)$_3$ alone or Al(OH)$_3$+sodium chloride complex adjuvant could effectively stimulate the production of antibody. However, compared with the Al(OH)$_3$ group alone, the Al(OH)$_3$+sodium chloride complex adjuvant group could produce higher IgG and IgG1 antibody titers, which reached the highest value when the mass fraction of sodium chloride was 3.6%.

(2) Determination of Cytokine IFN-γ

IFN-γ was determined by ELISA and flow cytometry. Details were as follows: the mice were killed one week after the last immunization and their spleens were removed. The splenic lymphocytes were stimulated with HBsAg in vitro and incubated in a $CO_2$ incubator for 72 h. The concentration of IFN-γ in the culture supernatant was determined by ELISA assay kit.

Figure 2:
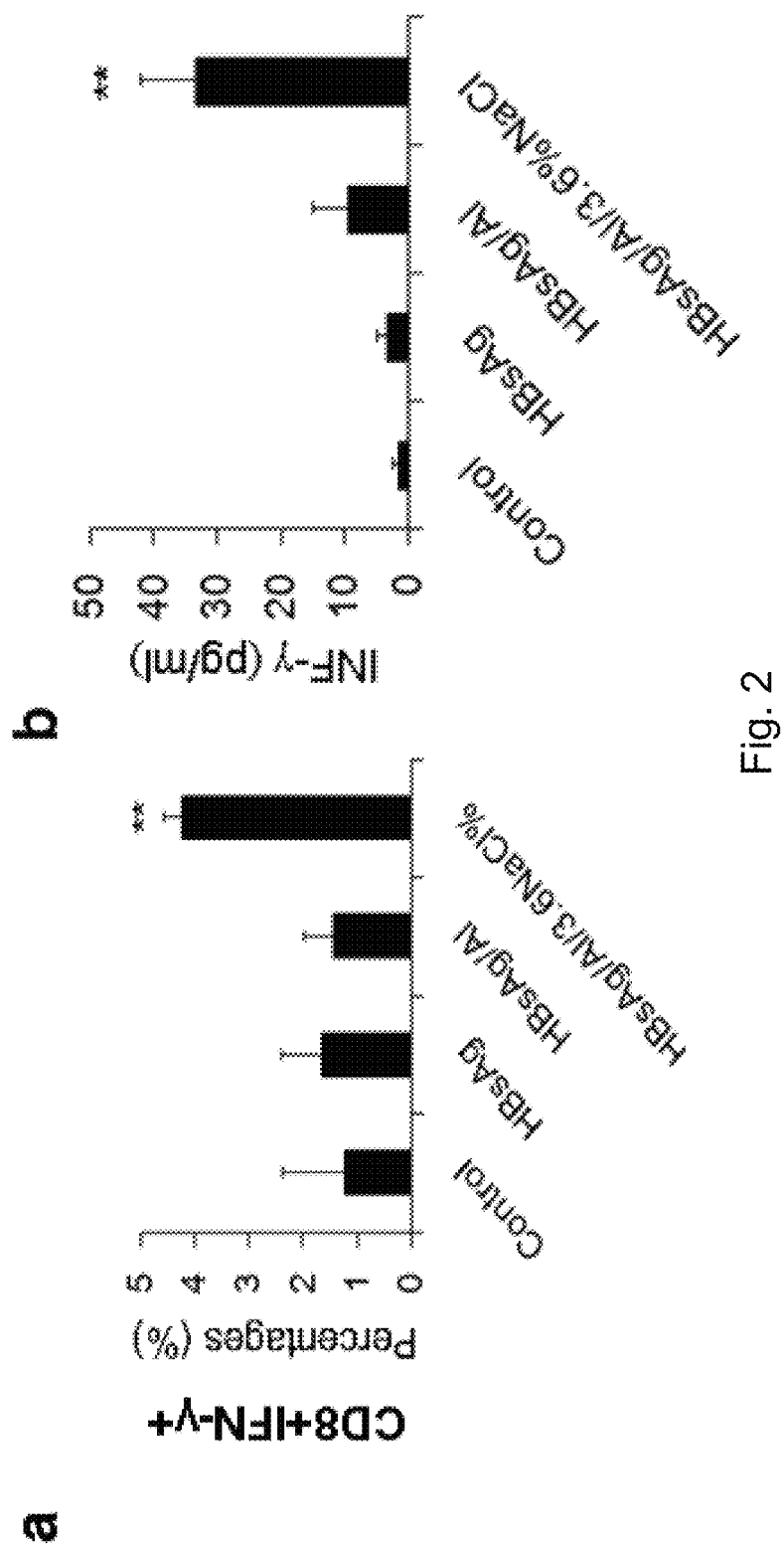
FIG. 2 shows the experimental result that the alhydrogel-sodium chloride immunologic adjuvant can enhance the specific cellular immune response of each group of mice to HBsAg in the HBsAg model.

The experimental results were shown in FIG. 2. It was found that significantly increased CD8$^+$ INF-γ secretion and cell immunity were observed in the hypersaline/aluminum adjuvant group in the HBsAg model. Flow cytometry and ELISA results were consistent.

Embodiment 3: Animal Immunity Test Taking Sodium Chloride as OVA Tumor Specific Antigen Adjuvant in the Invention Materials and reagents: aluminum hydroxide adjuvant, sodium chloride and OVA the same as embodiment 1; mice, ELISA kit for IFN-γ, lymphocyte separation medium, 70 μm nylon mesh filter and 24/96-well plate with round bottom the same as embodiment 2; mouse lymphatic cancer cells EG7 (ATCC, USA); and Na$_2$$^{51}$CrO$_4$ (PerkinElmer, USA).

(1) Preventive and Therapeutic Experiments on the Growth of Mice Syngeneic Tumor Based on Novel Adjuvant of the Invention Preventive experiment: the C57 mice were randomly divided into 4 groups: 1. Control; 2. OVA; 3. OVA/Al(OH)$_3$; 4. OVA/Al(OH)$_3$/3.6% NaCl. Of all the groups, as the tumor specific antigen, OVA was 5 μg and Al(OH)$_3$ was 125 μg; the ratio of OVA to Al(OH)$_3$ was 1:25 by weight; and sodium chloride was formulated at the concentration according to the grouping requirements. Each group had ten mice, which were subcutaneously injected with vaccine at left back side at week 0, 2 and 3 respectively. Mouse lymphoma cells (3×10$^6$/mouse) were subcutaneously inoculated on the right side on the 7$^{th}$ day after the last immunization, a mouse syngeneic tumor model was established, and the tumor volume of mice was measured every 3 days.

Therapeutic experiment: after mice were randomly divided into 4 groups, mouse lymphoma cells ($3\times10^6$/mouse) were subcutaneously inoculated on the right side until the tumor grew to be palpable (approximately 3 mm, 3-5 days after vaccination). Then, mice were subjected to subcutaneous immunotherapy at the dosage of each group mentioned in the preventive experiment, once a week, and three consecutive times. The tumor volume of mice was measured every 3 days.

Figure 5:
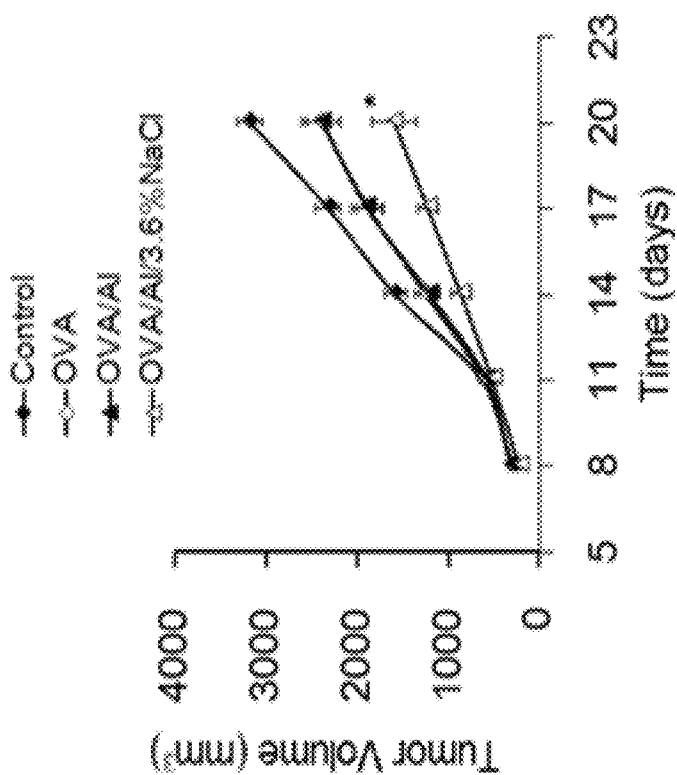
FIG. 5 shows that the alhydrogel-sodium chloride immunologic adjuvant can enhance the anti-tumor effect of vaccine in preventive and therapeutic tumor models.
Figure 5:
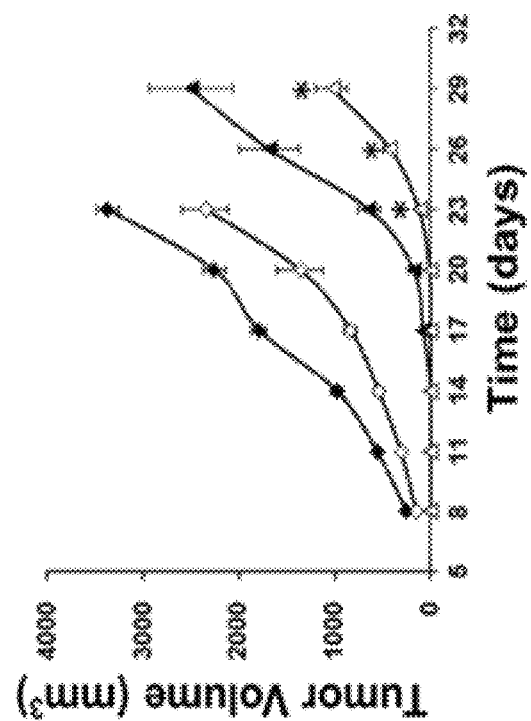

The preventive and therapeutic results were given in FIG. 5 respectively. The tumor growth was significantly inhibited in $Al(OH)_3$+sodium chloride complex adjuvant group compared with the control group (Control, OVA) and the $Al(OH)_3$ adjuvant vaccine group alone.

(2) Determination of Antibody Titer

Figure 3:
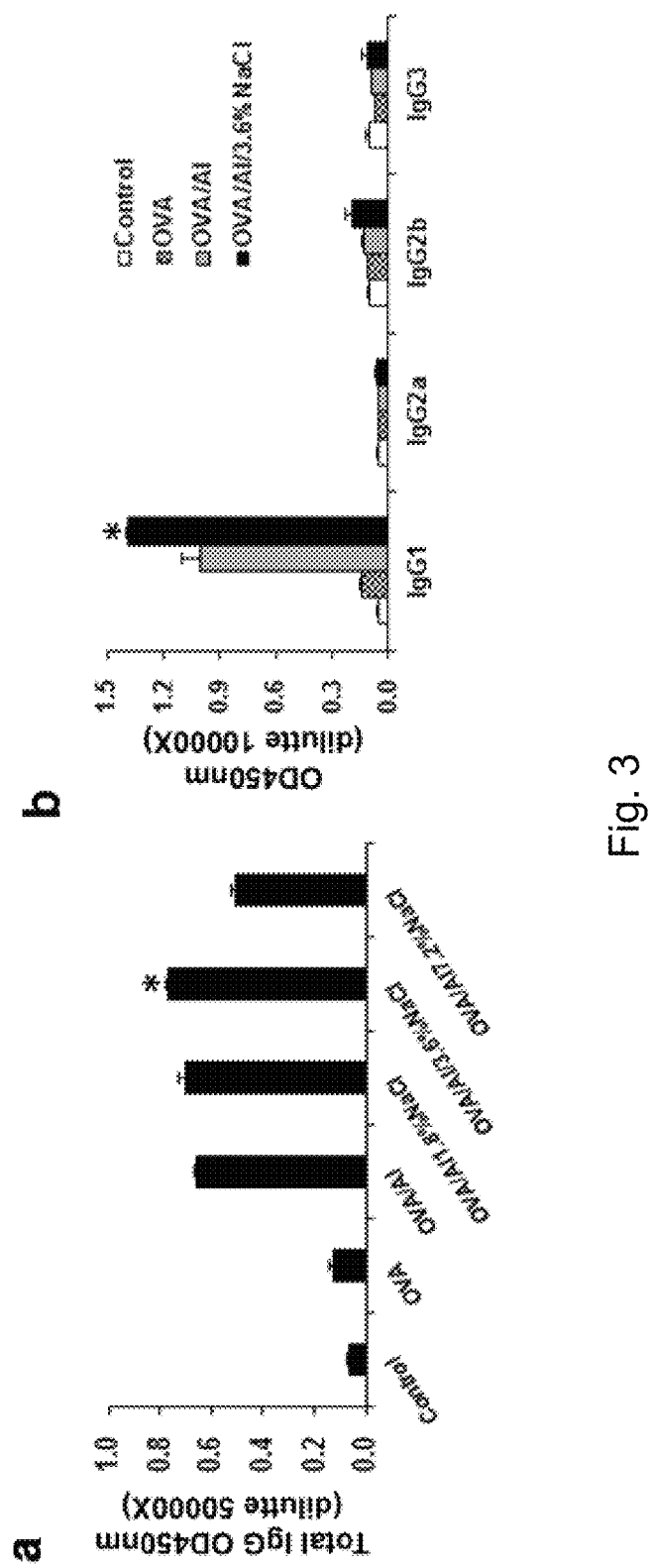
FIG. 3 shows the experimental result that the alhydrogel-sodium chloride immunologic adjuvant can enhance the serum antibody titer of each group of mice against OVA in the OVA model.

Experimental methods and groups were the same as embodiment 2: 1. Control; 2. OVA; 3. OVA/$Al(OH)_3$; 4. OVA/$Al(OH)_3$/1.8% NaCl 5. OVA/$Al(OH)_3$/3.6% NaCl 6. OVA/$Al(OH)_3$/7.2% NaCl. Of all the groups, the OVA was 5 μg and $Al(OH)_3$ was 125 μg; the ratio of OVA to $Al(OH)_3$ was 1:25 by weight; and sodium chloride was prepared at the concentration according to the grouping requirements. Each group had five mice. The mice serum was collected on the $7^{th}$ day after the last immunization and the antibody titer in each group of mice was assayed by the self-coated ELISA. The antibody absorbance detection results of each group were shown in FIG. 3. The OVA group alone could hardly produce antibodies. The group using $Al(OH)_3$ alone or $Al(OH)_3$+sodium chloride complex adjuvant can effectively stimulate the production of antibody. However, compared with the $Al(OH)_3$ group alone, the $Al(OH)_3$+sodium chloride complex adjuvant group could produce higher IgG and IgG1 antibody titers, which reached the highest value when the mass fraction of sodium chloride was 3.6%.

(3) Determination of Cytokine IFN-γ

IFN-γ was determined by the self-coated ELISA kit (eBioscience) and flow cytometry. Details were as follows: the mice were killed one week after the last immunization and their spleens were removed. The splenic lymphocytes were stimulated with 5 μg of different OVA peptide fragments and incubated in a $CO_2$ incubator for 72 h. The concentration of IFN-γ in the culture supernatant was determined by ELISA assay kit. Cells were used for INF-γ and specific OVA-Tetramer experiments.

Figure 4:
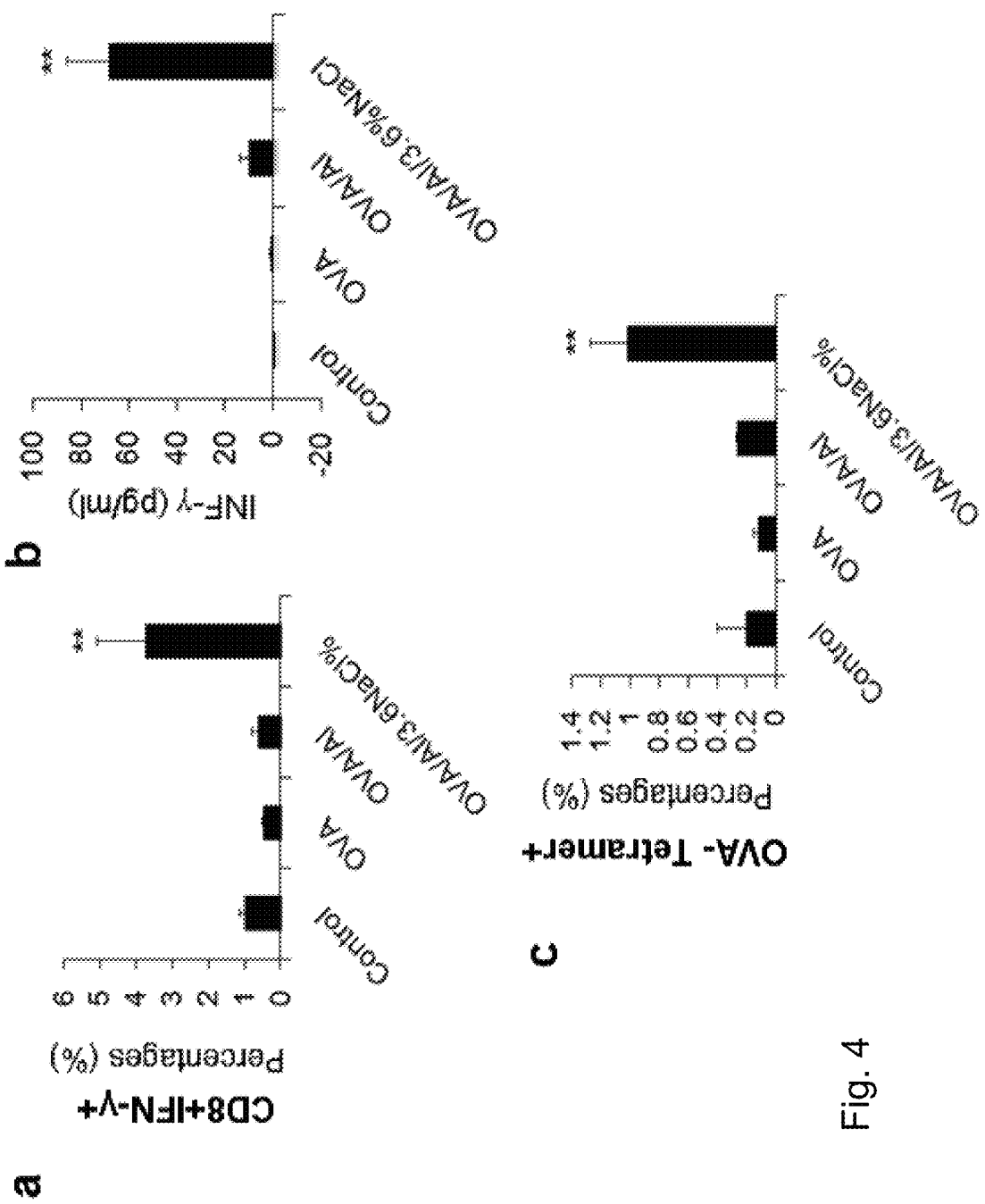
FIG. 4 shows the experimental result that the alhydrogel-sodium chloride immunologic adjuvant can enhance the specific cellular immune response of each group of mice to OVA in the OVA model.

The experimental results were given in FIG. 4. It was found that $CD8^+INF$-γ secretion increased significantly in the hypersaline/aluminum adjuvant group in the OVA model. Flow cytometry and ELISA results were consistent. In addition, FIG. 4c represented an increased positive percentage of specific OVA-Tetramer, which indicating that $Al(OH)_3$+sodium compound adjuvant indeed induces specific cellular immunity.

(4) Novel Adjuvant Vaccine of the Invention Stimulates the Killing Function of Tumor-Specific Cytotoxic T Lymphocytes The killing function of cytotoxic T lymphocytes was detected by $^{51}Cr$ releasing test.

Mice were immunized as described in the preventive model. Three mice were randomly taken from each group 7 days after the last immunization. Mice were dissected in the aseptic condition to separate their splenic lymphocytes, which were adjusted to the concentration of $1\times10^7$/ml, then effector cells were obtained.

Collect tumor cells E.G7 cultured in vitro, and count. Adjust the concentration of tumor cells to $1\times10^7$/ml based on the medium. Take 200 μl of cells, add 100 μci $Na_2^{51}CrO_4$, incubate at 37° C. for 2 h, label, and wash for three times. After cell counting, adjust the concentration of cells to $0.5\times10^5$/ml, and obtain $^{51}Cr$ labeled tumor cells, i.e. target cells. Add the target cell suspension to a 96-well plate with round bottom, 100 μl for each well, add effector cells to triplicate wells according to the different proportions in Table 1:

TABLE 1

| | Ratio of effector cells to target cells | | | | Natural release group | Maximum release group |
|---|---|---|---|---|---|---|
| | 200:1 | 100:1 | 50:1 | 25:1 | | |
| $^{51}Cr$ target cells ($0.5\times10^5$/ml) | 100 μl | 100 μl | 100 μl | 100 μl | 100 μl | 100 μl |
| Effector cells ($1\times10^7$/ml) | 100 μl | 50 μl | 25 μl | 12.5 μl | 0 | 0 |
| Medium (1640, 10% FBS) | 0 | 50 μl | 75 μl | 87.5 μl | 100 μl | 0 |
| 1% Triton X-100 | 0 | 0 | 0 | 0 | 0 | 100 μl |
| Total volume | 200 μl | 200 μl | 200 μl | 200 μl | 200 μl | 200 μl |

Add 100 μl of $^{51}Cr$ labeled tumor cells to each well, add 100 μl of medium to the natural release group and 100 μl of 1% Triton X-100 to the maximum release group respectively. Centrifuge in a 96-well plate horizontal centrifuge rotor at 1500 rpm/min for 30 seconds, and incubate in a 5% $CO_2$ incubator at 37° C. 4-6 h later, centrifuge in a 96-well plate horizontal centrifuge rotor at 1500 rpm/min for 5 min, pipette 100 μl of supernatant from each well, and detect the cpm value by Backmen550B γ counter. CTL kill rate formula: kill rate %=[(experimental group cpm−natural release group cpm)/(control group cpm−natural release group cpm)]×100%.

Figure 6:
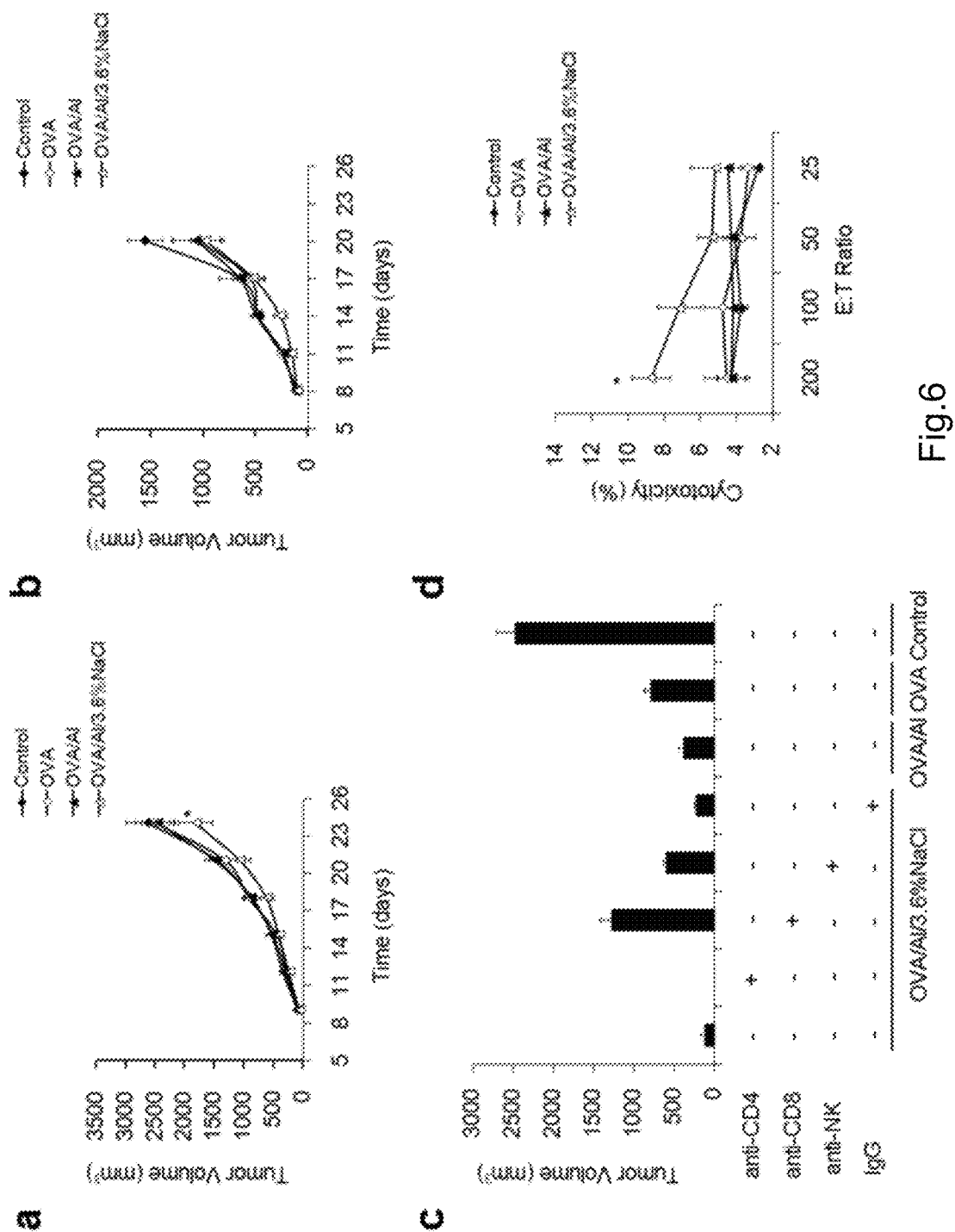
FIG. 6 shows the experimental result that the alhydrogel-sodium chloride immunologic adjuvant has the anti-tumor effect as a result of inducing specific killer CD8+T cells (CTL reaction).

The experimental results were given in FIG. 6d, wherein the $Al(OH)_3$+sodium chloride complex adjuvant group (OVA/Al/3.6% NaCl) can induce specific CTL response to tumor cells more effectively than the control group (Control, OVA) or the $Al(OH)_3$ adjuvant group alone (OVA/Al).

(5) Mice Adoptive Therapy Experiment and Antibody Blocking Experiment Induced by Novel Adjuvant Vaccine Immunization of the Invention EG7 cells ($3\times10^6$/mouse) were injected subcutaneously into the right dorsal flank of mice, a mouse syngeneic tumor model was established, and mice were randomly divided into 4 groups, five for each group. Cellular adoptive therapy: the splenic lymphocytes obtained from the preventive experiment were injected through the caudal vein the day before, one day and three days after the establishment of mouse syngeneic tumor model, $10^7$ cells/mouse, and a total of 3 times. The change of tumor volume in mice was observed every three days.

Serum adoptive therapy: the serum obtained from the preventive experiment was injected through the caudal vein the day before, and in three consecutive weeks after the establishment of mouse syngeneic tumor model, 250 μl/mouse, and twice a week. The change of tumor volume in mice was observed every three days.

Antibody blocking: anti-CD4, CD8, NK monoclonal antibody or control non-specific RAT antibody were administrated through intraperitoneal injection the day before and during the immunization, twice a week, and in three consecutive weeks. After immunization, mice were inoculated with EG.7 cells and mouse tumor growth curve was monitored every 3 days.

The experimental results given in FIG. 6a, b and c reveal that serum adoptive therapy had hardly anti-tumor effect, while the cellular adoptive therapy $Al(OH)_3$+sodium chloride complex adjuvant group (OVA/Al/3.6% NaCl) had a significant antitumor effect. In addition, anti-tumor effect was not affected by blocking CD4+T cells, but blocking CD8+T cells almost completely counteracted the antitumor effect of compound immunologic adjuvant, which indicating that the anti-tumor effect of hypersaline/aluminum compound adjuvant was mainly attributed to CD8+killer T lymphocyte induced by it rather than CD4+T lymphocyte.
(6) Change of Memory T Lymphocytes and Mice Tumor Microenvironment Due to Novel Adjuvant Vaccine Immunization of the Invention The splenic lymphocytes or tumors of mice in preventive or therapeutic vaccine experiment were prepared into a single cell suspension, and the changes of various immune cell populations were detected by flow cytometry.

Figure 11:
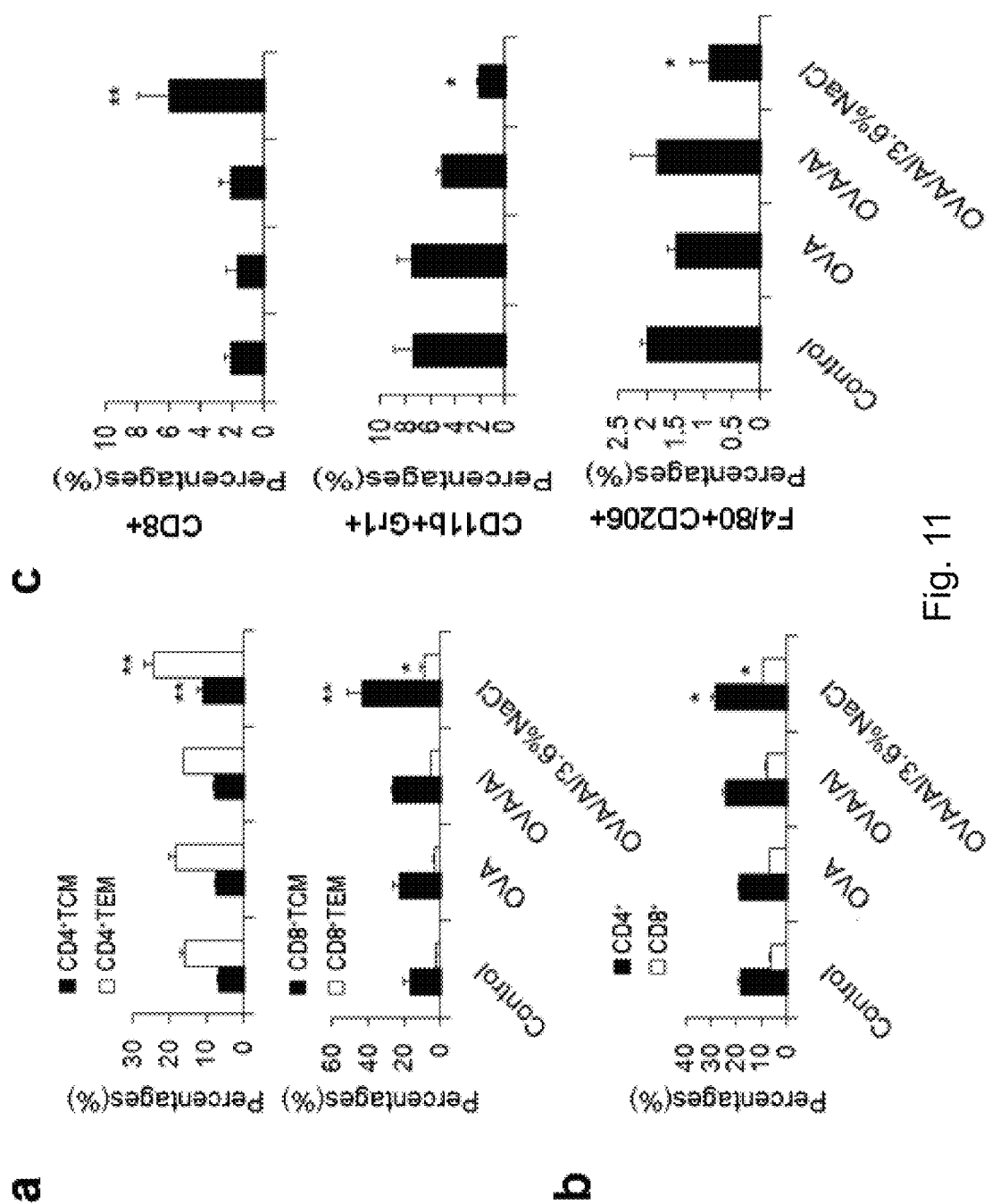
FIG. 11 shows the experimental result that the alhydrogel-sodium chloride immunologic adjuvant can increase memory T cells and improve the tumor microenvironment.

The experimental results of memory T lymphocytes shown in FIG. 11a reveal that $Al(OH)_3$+sodium chloride complex adjuvant immunization could significantly increase central and effector CD4+CD8+T lymphocytes. For the tumor microenvironment, the results given in FIGS. 11b and c reveal that $Al(OH)_3$+sodium chloride complex adjuvant not only increased the infiltration of CD8+ killer T lymphocytes in tumor tissues, but also reduced the number of immunosuppressive MDSC and M2 macrophages.
(7) Novel Sodium Chloride Adjuvant of the Invention Can Promote the Functions of DC In Vitro As the main antigen-presenting cell, DC play an indispensable role in the immune response of vaccines. So we studied the effect of high NaCl concentration on the functions of DC in vitro.

Figure 7:
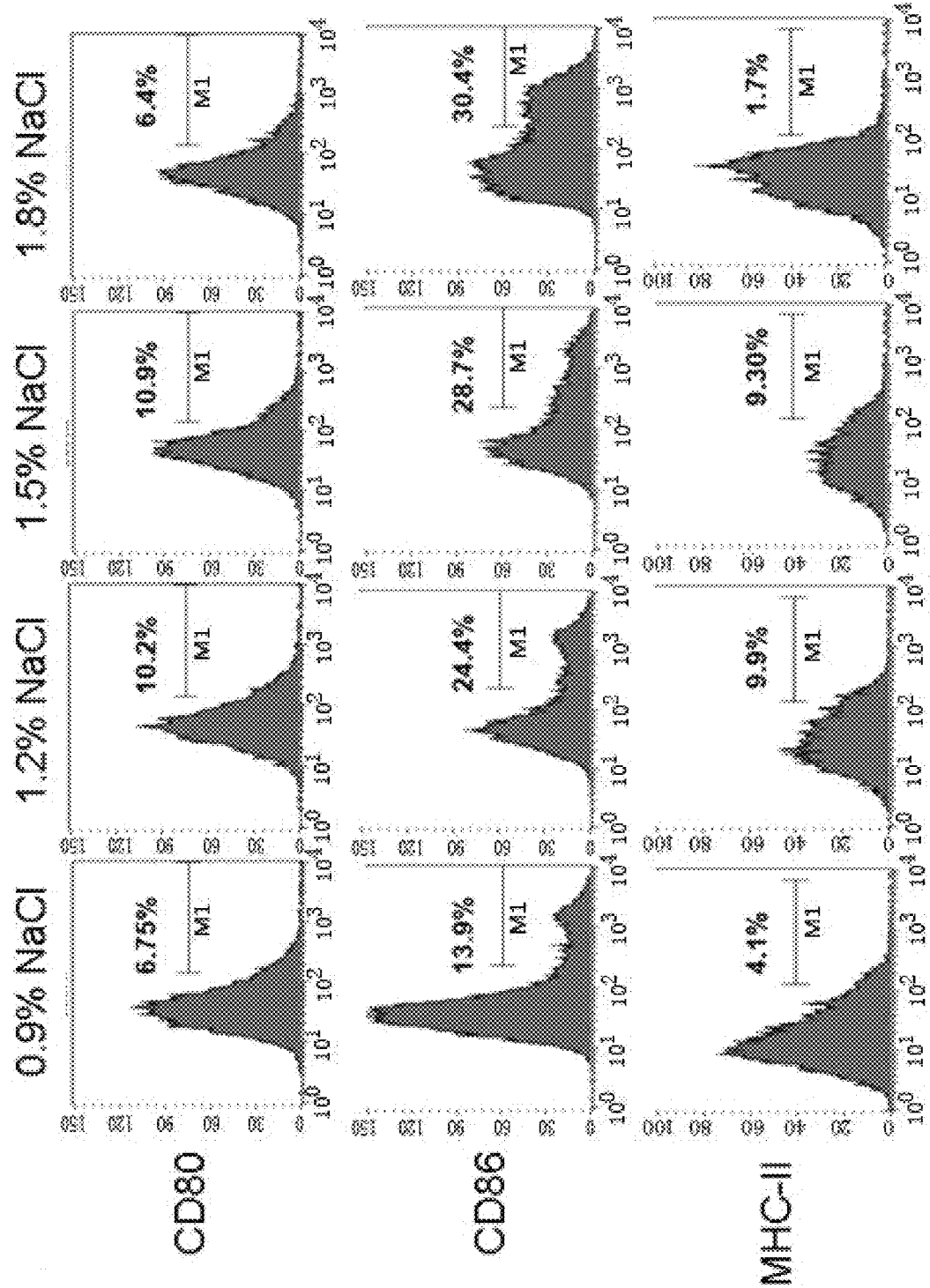
FIG. 7 shows the experimental result that the hypertonic sodium chloride can promote the maturation of Dendritic cell (DC) in vitro.

The experimental groups were shown in FIG. 7. C57BL/6 mouse primary bone marrow DC was prepared by the classical method. Differentiate and stimulate the cells with cytokines such as GM-CSF for 6 days, collect and continue to culture in the medium containing different mass fractions of sodium chloride for 48 h, detect the proportion of mature molecules such as CD80 and CD86 by flow cytometry, and assay the secretion of inflammatory cytokines in supernatant by ELISA. Meanwhile, collect and lyse part cells to prepare RNA, and detect the mRNA level of associated inflammatory molecules by RT-PCR. In addition, culture DC in a medium with different mass fraction 1 h, and detect the phagocytosis of associated antigen by fluorescence microscope or flow cytometry.

Figure 8:
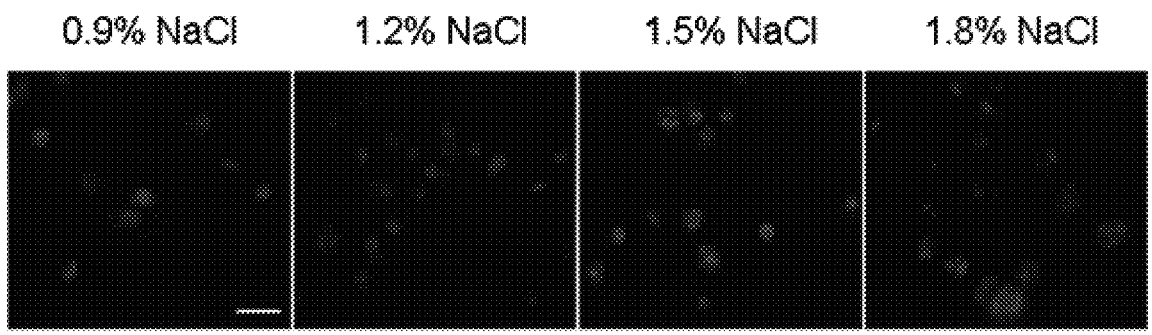
FIG. 8 shows the experimental result that the hypertonic sodium chloride can promote antigen phagocytosis of DC in vitro.
Figure 8:
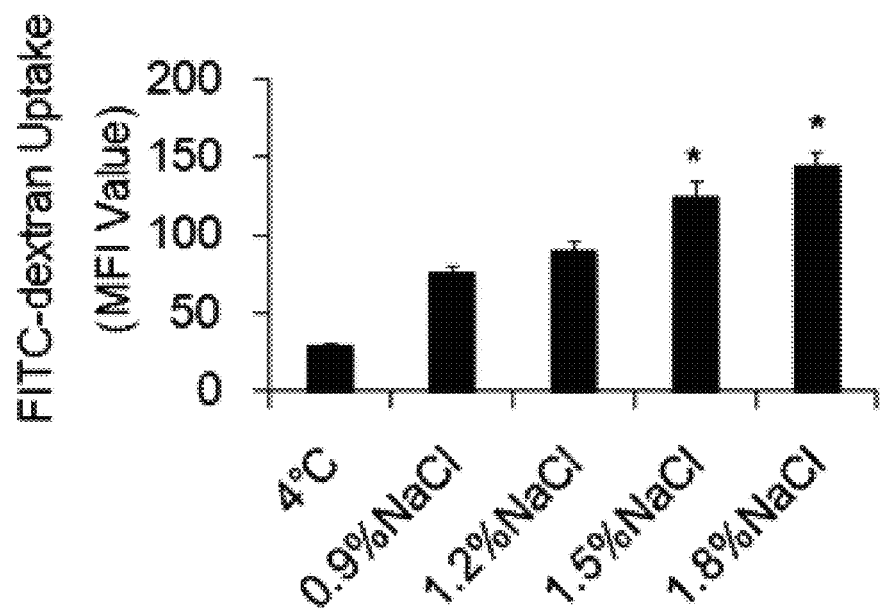
Figure 9:
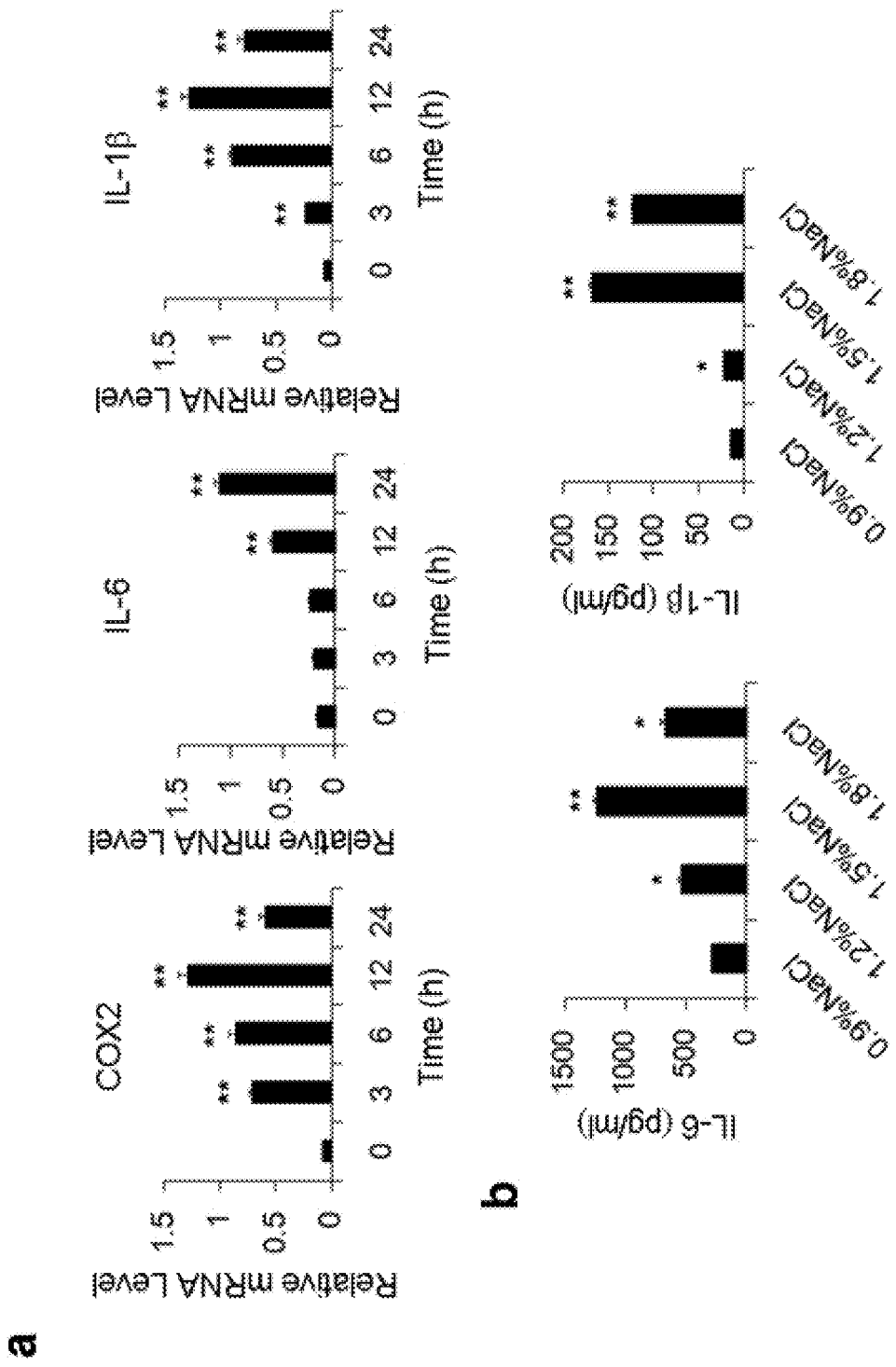
FIG. 9 shows the experimental result that the hypertonic sodium chloride can promote the secretion of inflammatory cytokines in DC in vitro.

As shown in FIG. 7, in vitro stimulation of DC with high NaCl concentration could promote its maturation and increase the expression of molecules such as CD80, CD86 and MHCII on its surface. As shown in FIG. 8, high NaCl concentration also could promote the DCs' phagocytosis of the antigen. As shown in FIG. 9, it could further increase the release of inflammatory cytokines IL6 and IL1b in mRNA and protein levels.

Next, we continue to explore whether the cell-specific immune response induced by high NaCl concentration is related to the cross antigen presentation of DC.

Figure 10:
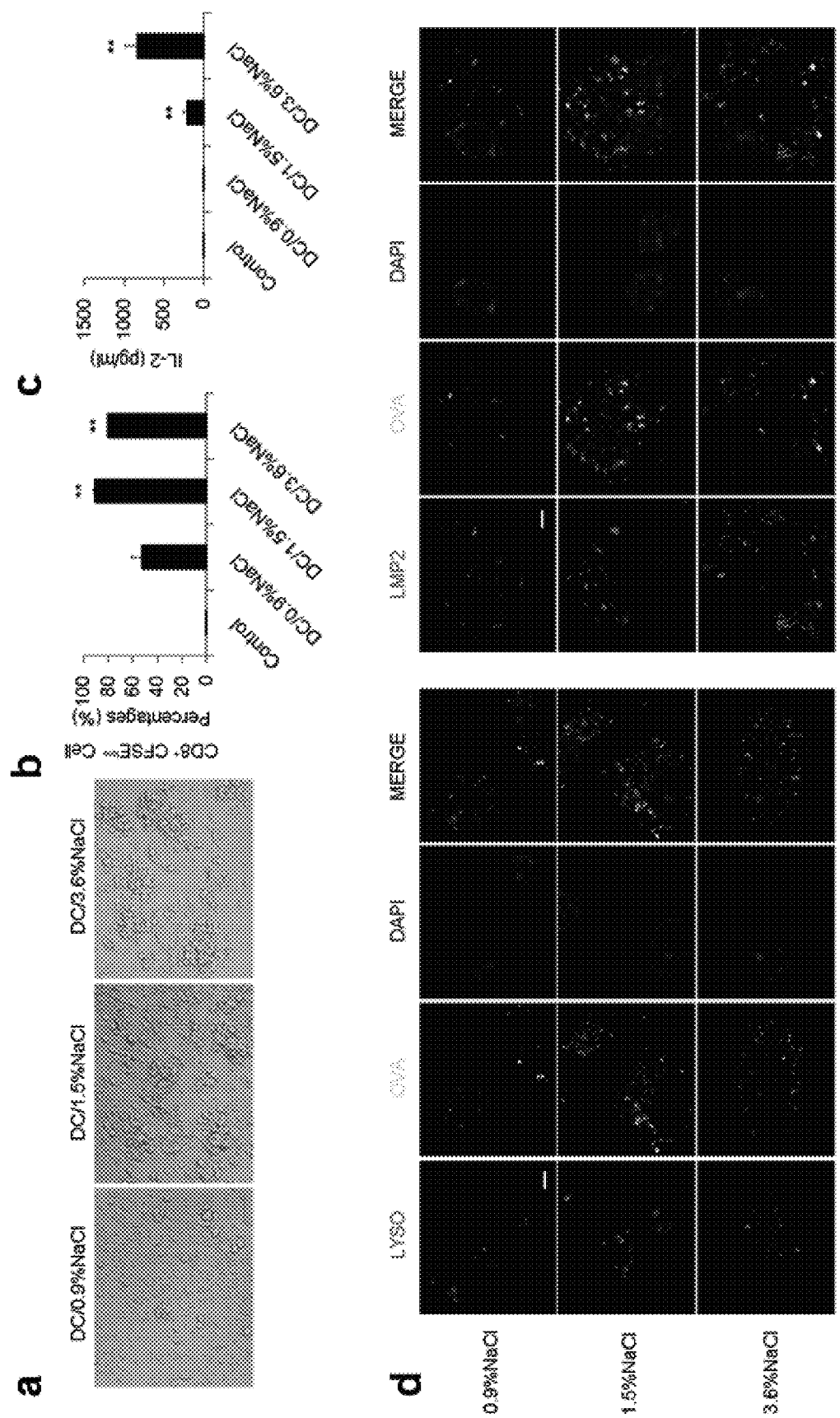
FIG. 10 shows the experimental result that the hypertonic sodium chloride can promote the antigen cross presentation of DC in vitro.

DC/T lymphocyte co-culture experiment: the experimental group was shown in FIG. 10. Co-culture DC stimulated by high NaCl concentration and OVA antigen in vitro and CFSE-labeled CD8+T lymphocytes from OT-1 transgenic mouse for 2-3 days, observe the formation of CLUSTER under white light of the microscope, detect the proliferation of CFSE-labeled CD8+T lymphocytes by flow cytometry, and detect the secretion of IL2 in the collected culturesupernatant by ELISA.

Immunofluorescence co-localization experiment: the experimental group, ibid. Fix and permeabilize DC stimulated by high NaCl concentration and fluorescent labeled OVA in vitro, and stain with organelle fluorescent protein markers of proteasome and lysosome, and observe under the confocal microscopy.

According to FIGS. 10a, b and c, DC/T lymphocyte co-culture experiment reveals that the DC treated by high NaCl concentration could uptake and present the OVA antigen molecule to the specific CD8+T lymphocytes, and induce their proliferation and secretion of IL2. According to FIG. 10d, the immunofluorescence co-localization experiment also reveals that OVA was mostly degraded by proteasome rather than lysosome in the DC treated by high NaCl concentration. Therefore, high NaCl concentration can significantly improve the cross antigen presentation of DC.

Embodiment 4: Animal Immunity Test Taking Sodium Chloride as Bacterial Vaccine Adjuvant in the Invention Materials and reagents: aluminum hydroxide adjuvant, sodium chloride, *Staphylococcus aureus* (S.a) or *Pseudomonas aeruginosa* (P.a), pertussis and diphtheria toxoid the same as embodiment 1; C57BL/6 mice purchased from Beijing Vital River Laboratory Animal Technology Co., Ltd.; ELISA kit for IFN-γ (eBioscience, USA), lymphocyte separation medium (Dakewe Biotech Co., Ltd.); 70 μm nylon mesh filter (Becton, Dickinson and Company, USA); and 24-well plate with round bottom (NUNK).

The experimental animals were immunized in groups as follows: 1. Control; 2. S.a or P.a; 3. S.a or P.a/$Al(OH)_3$; 4. S.a or P.a/$Al(OH)_3$/3.6% NaCl. The specific immunization plan was as follows: centrifuge the bacteria solution in enlarged cultivation and wash; fix and inactivate with 1% paraformaldehyde, wash, and re-suspend in PBS. Each group had five mice. Immunize subcutaneously for 3 times at week 0, 2, and 3, with the bacteria solution of 0.05 OD($1\times10^6$ CFU/200 μL), 0.5 OD($1\times10^7$ CFU/200 μL) and 2.5 OD($5\times10^7$ CFU/200 μL) respectively; collect serum for the purpose of antibody detection after each immunization.

Figure 12:
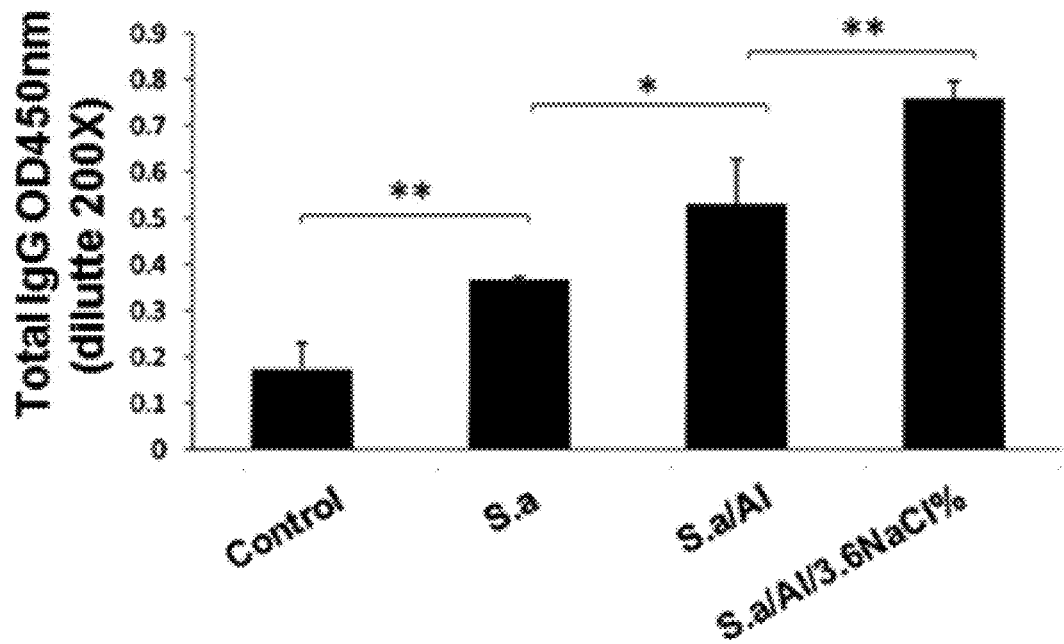
FIG. 12 shows the experimental result that the alhydrogel-sodium chloride immunologic adjuvant can enhance the serum antibody titer of each group of mice in the *Staphylococcus aureus* model.
Figure 13:
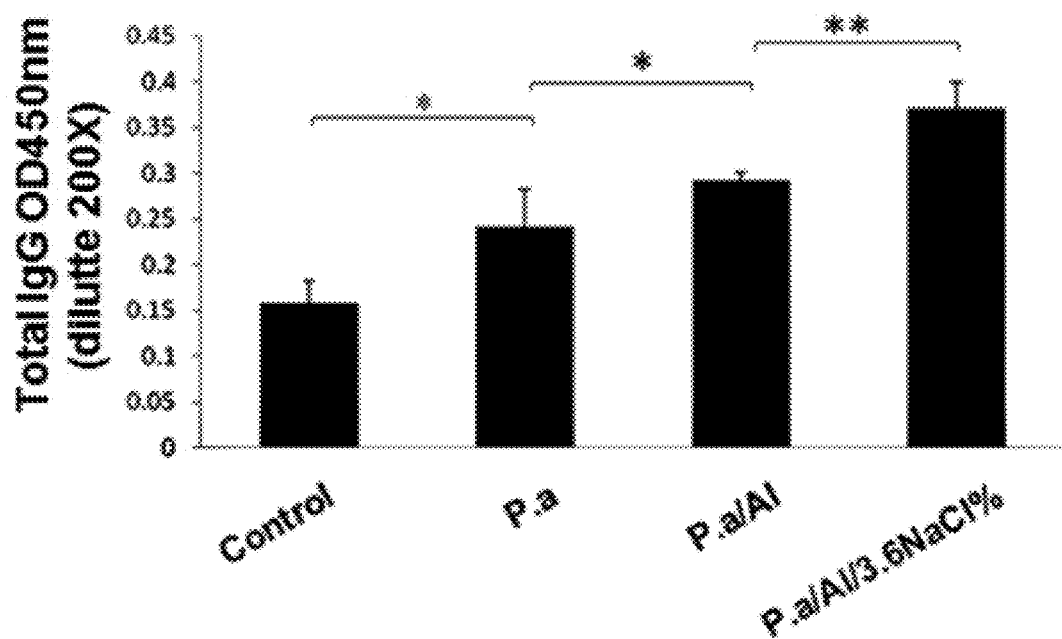
FIG. 13 shows the experimental result that the alhydrogel-sodium chloride immunologic adjuvant can enhance the serum antibody titer of each group of mice in the *Pseudomonas aeruginosa* model.

Detection of antibody titer: specific IgG antibody titers against different bacteria in the serum of mice in each group were detected by ELISA using a self-coated 96-well plate coated with $1\times10^7$ CFU/100 μL whole bacteria antigen. The experimental results given in FIG. 12 reveal that *Staphylococcus aureus* specific antibody was detected, $Al(OH)_3$ adjuvant could help increase the antibody level and hypersaline $Al(OH)_3$ adjuvant had better effect. Likewise, *Pseudomonas aeruginosa* specific antibody was detected. The experimental results given in FIG. 13 reveal that $Al(OH)_3$ adjuvant could help increase the antibody level and hypersaline $Al(OH)_3$ adjuvant had better effect. The pertussis or diphtheria toxin experimental animals were grouped the same as *Staphylococcus aureus* and *Pseudomonas aeruginosa*. Of all the groups, pertussis or diphtheria toxin was 1 μg and $Al(OH)_3$ was 25 μg; the ratio of pertussis or diphtheria toxin to $Al(OH)_3$ was 1:25 by weight; and sodium chloride was prepared at the concentration according to the grouping requirements. Each group had five mice. Muscle immunity was performed at week 0, 2 and 3, and serum was collected each week for ELISA test of serum antibody. The experimental results were similar to *Staphylococcus aureus* and *Pseudomonas aeruginosa*, i.e. the alhydrogel-sodium chloride immunologic adjuvant can induce diphtheria toxin to produce specific antibody, and increase the production of antibody by about 48%. Also, the alhydrogel-sodium chloride immunologic adjuvant can induce the production of pertussis toxin with an increase of approximately 45%.

The invention claimed is:

1. A compound immunologic adjuvant comprising alhydrogel and sodium chloride, wherein a final mass fraction of the sodium chloride is 2.7%-4.5%.

2. The compound immunologic adjuvant according to claim 1, wherein the final mass fraction of the sodium chloride is 3.6%.

3. The compound immunologic adjuvant according to claim 1, wherein a particle size of the alhydrogel ranges from 1 μm to 10 μm.

4. An immunologic adjuvant-antigen complex, characterized by comprising an antigen and the compound immunologic adjuvant according to claim 1.

5. The immunologic adjuvant-antigen complex according to claim 4, wherein a ratio of the antigen to the alhydrogel in the compound immunologic adjuvant is 1:1-100 by weight.

6. The immunologic adjuvant-antigen complex according to claim 5, wherein the ratio of the antigen to the the alhydrogel is 1:5-50 by weight.

7. The immunologic adjuvant-antigen complex according to claim 4, wherein the antigen is at least one of a tumor antigen, a virus antigen or a bacterial antigen.

8. The immunologic adjuvant-antigen complex according to claim 7, wherein the tumor antigen is selected from at least one of OVA tumor model antigen, NY-ESO-1, human melanoma-associated antigen gP100, melanoma antigen mage-1 or carcinoembryonic antigen.

9. The immunologic adjuvant-antigen complex according to claim 7, wherein the virus antigen is at least one member selected from the group consisting of hepatitis B virus antigen, hepatitis A virus antigen, hepatitis C virus antigen, poliovirus antigen, rabies virus antigen, yellow fever virus antigen, HIV antigen, measles antigen, mumps antigen, rubella antigen, chicken pox antigen, rotavirus antigen, Japanese encephalitis antigen, papillomavirus antigen, epidemic hemorrhagic fever virus antigen and plague virus antigen.

10. The immunologic adjuvant-antigen complex according to claim 7, wherein the bacterial antigen is at least one member selected from the group consisting of *Staphylococcus aureus* antigen, *Pseudomonas aeruginosa* antigen, pertussis antigen, diphtheria antigen, *Haemophilus influenzae* antigen, *Neisseria meningitidis* antigen, tetanus toxoid antigen, *Streptococcus hemolyticus* antigen, *Streptococcus* non-*hemolyticus* antigen, *Pneumococcus* antigen, *Tubercle bacillus* antigen, *Bacillus anthracis* antigen, *Vibrio cholerae* antigen, *Leptospira* antigen and *Helicobacter pylori* antigen.

11. A method for preparing the immunologic adjuvant-antigen complex according to claim 4, said method comprising the following steps:
   a. diluting or dissolving the antigen in water;
   b. adding the sodium chloride, and uniformly mixing;
   c. adding the alhydrogel, and uniformly mixing.

12. A method for preparing the immunologic adjuvant-antigen complex according to claim 4, said method comprising the following steps:
   a. adding the sodium chloride to an alhydrogel adjuvant to prepare a stock solution for a hypertonic alhydrogel compound adjuvant;
   b. diluting or dissolving the antigen in water;
   c. adding the hypertonic alhydrogel compound adjuvant, and uniformly mixing.

13. A method for preparing a vaccine, said method comprising combining sodium chloride and water fro injection and allowing a mass fraction of sodium chloride to reach 2.7%-4.5% before the vaccine is used, wherein said method comprises the following steps:
   adding the water for injection and the sodium chloride to an antigen, then adding an alhydrogel adjuvant, and allowing the mass fraction of sodium chloride in the prepared vaccine to reach 2.7%-4.5% before the vaccine is used;
   or directly dissolving the antigen in water, adding a hypertonic alhydrogel stock solution, and allowing the mass fraction of sodium chloride in the prepared vaccine to reach 2.7%-4.5%;
   or directly adding an adjuvant of sodium chloride in the preparation process, and allowing the mass fraction of sodium chloride in the prepared vaccine to reach 2.7%-4.5% before injection, if the vaccine to be prepared already contains the antigen and the alhydrogel.

14. A method for preparing a vaccine, said method comprising combining sodium chloride and water for injection, wherein a final mass fraction of the sodium chloride in the prepared vaccine is 3.6%.

15. The method for preparing a vaccine according to claim 13, wherein a ratio of the antigen to the alhydrogel in the prepared vaccine is 1:1-100 by weight.

16. The method for preparing a vaccine according to claim 15, wherein the ratio of the antigen to the the alhydrogel in the prepared vaccine is 1:5-50 by weight.

* * * * *

UNITED STATES PATENT AND TRADEMARK OFFICE
CERTIFICATE OF CORRECTION

PATENT NO. : 10,869,922 B2
APPLICATION NO. : 16/300295
DATED : December 22, 2020
INVENTOR(S) : Xiawei Wei, Min Luo and Yuquan Wei Page 1 of 1

It is certified that error appears in the above-identified patent and that said Letters Patent is hereby corrected as shown below:

On the Title Page

Item (30) Foreign Application Priority Data, the application number "(CN) ................... 2016 1 0318724" should read -- (CN) ................... 2016 1 0318724.X --.

Signed and Sealed this
Sixteenth Day of February, 2021

Drew Hirshfeld
*Performing the Functions and Duties of the
Under Secretary of Commerce for Intellectual Property and
Director of the United States Patent and Trademark Office*